United States Patent [19]

Wilson et al.

[11] Patent Number: 5,308,606
[45] Date of Patent: * May 3, 1994

[54] METHOD OF TREATING AND/OR DIAGNOSING SOFT TISSUE TUMORS

[75] Inventors: David A. Wilson, Richwood; R. Keith Frank; Joseph R. Garlich, both of Lake Jackson; Jaime Simon, Angleton, all of Tex.

[73] Assignee: The Dow Chemical Company, Midland, Mich.

[*] Notice: The portion of the term of this patent subsequent to Jan. 30, 2007 has been disclaimed.

[21] Appl. No.: 648,663

[22] Filed: Jan. 30, 1991

[51] Int. Cl.$^5$ .................. A61K 43/00; A61K 49/02
[52] U.S. Cl. ................................................ 424/1.65
[58] Field of Search ................ 424/1.1; 534/10, 14

[56] References Cited

U.S. PATENT DOCUMENTS 421,452  10/1890  Wilson et al. .
4,897,254  1/1990  Simon et al. .
4,898,724  2/1990  Simon et al. .

OTHER PUBLICATIONS

*Intl. J. Nucl. Med. Biol.* 8, 249-255 (1981), G. S. Johnson.
*Acta Radiol.* (*Ther. Phys. Biol.*) 11, 566-575 (1972), D. Emrich et al., Department of Medicine and Radiology, Division of Nuclear Medicine, U. of Gottingen, Germany.
*Intl. J. Nucl. Med. Biol.* 11(2), 195-201 (1984), A. Ando et al.
*Prog. Radiopharmacol.* (*Proc. Eur. Symp. Radiopharmacol.*) 1, 63-73 (1979), D. M. Taylor et al.
*Intl. J. Nucl. Med. Biol.* 10 (4), 257-261 (1983), R. L. Hayes.
*Intl. J. of Med. Biol.* 2, 45-48 (1975) M. V. Merrick.
*Intl. J. Nucl. Med. Biol.* 2, 44-45 (1975), J. C. Sullivan.
*Intl. J. of Med. Biol.* 10(4), 251-256, (1983), J. M. Woolfendewjm et al.
*Biochem. Archives* 4, 69-75 (1988), J. W. Tse et al.
*Eur. J. Nucl. Med.* 13, 432-438 (1987), J. Harvey Turner.
*Intl. J. Nucl. Med.* 30, 202-208 (1989), J. W. Tse.
*Chem. Pharm. Bull* 30(7), 2529-2533 (1982), K. Karube et al.
*Intl. J. App. Rad. and Isotopes* (14), 129-135 (1963), B. Rosoff et al.

*Primary Examiner*—Robert L. Stoll
*Assistant Examiner*—John M. Covert
*Attorney, Agent, or Firm*—Karen L. Kimble

[57] ABSTRACT

A method for therapeutic and/or diagnostic treatment of soft tumor carcinoma in mammals using certain metals or particle-emitting radionuclides complexed with hydroxyethylethylenediaminetriacetic acid is described.

14 Claims, No Drawings

METHOD OF TREATING AND/OR DIAGNOSING SOFT TISSUE TUMORS

This invention concerns a method of treating and/or diagnosing soft tissue tumors in mammals with metal-ligand complexes, and their formulations.

BACKGROUND OF THE INVENTION

Metal ligand complexes are routinely used for medicinal applications. For example, gadolinium complexes (gadolinium-diethylenetriaminepentaacetic acid. Gd-DTPA) are used to enhance the quality of magnetic resonance imaging. Gd-DTPA has been utilized in studying abnormalities of the gastrointestinal tract, liver, and kidneys as well as visualizing heart infarcts. [See I. K. Adzaml., *J. Nucl. Med.* 32, 139 (1989).] When radioactive metal ions are used, diagnostic imaging or therapy can be the end objective. Thus $^{99m}$Tc, a pure gamma emitter, in the form of a metal ligand complex is routinely used as a diagnostic agent. In some cases, such as the use of $^{99m}$Tc-DTPA, injection of the complex into the bloodstream does not result in the radionuclide localizing in any tissue. Instead, the radionuclide is eliminated from the body by the kidneys into the urine. In other cases, the radionuclide does localize in desired specific organs or tissues. Thus specific $^{99m}$Tc-phosphonic acid complexes localize in bone [*Radiology* 149, 823-828 (1983)] and one of the uses of $^{99m}$Tc-phosphonic acid complexes is the detection of calcific tumors.

More recently, similar chemistry has been used to deliver particle emitting radionuclides to calcific type tumors. The aim of these agents is to diliver a therapeutic radiation dose to the site of the tumor. This type of agent takes advantage of fast bone turnover for its localization. Thus Deutsch et al. [*Radiology* 166, 501-507 (1988)] have proposed a rhenium-dipho for the treatment of bone cancers and Simon et al. (U.S. Pat. No. 4,898,724) have taught the use of rare earth radionuclides with aminophosphonic acids towards the same objective.

The specific delivery of metals to soft tissue (i.e. non-calcific) tumors has also been an objective for scientists. Anghilery in *Nuklearmedizin* 23, 9-14 (1984) describes the difficulty in achieving this objective when he states that "there are no fundamental qualitative differences in the structural, biochemical and functional characteristics of a tumor compared to the normal cell." With the advent of monoclonal antibodies, a plethora of activity has emerged using these proteins to deliver radionuclides to soft tissue tumors [e.g. A. R. Fritzberg et al., *Pharm. Res.* 5(6), 325 (1988)]. Bifunctional chelating agents were developed to bind the metal ions to the monoclonal antibody through a chelating agent (which metal-ligand-antibody system is termed a "conjugate") and many such conjugates have emerged. Some conjugates use gamma emitters such as $^{99m}$Tc or $^{111}$In for imaging (see for example U.S. Pat. Nos. 4,454,106, 3,994,966, 4,662,420 and 4,479,930); and other proposed conjugates with particle emmiters such as $^{67}$Cu [see for example J. C. Roberts et al., *Appl. Rad. Isotopes* 40(9), 775 (1989)] or $^{90}$Y [see for example *J. Nucl. Med.* 26(5), 503 (1985)] for therapy. It was believed that the use of the conjugates provided the answer to the site specific delivery of a metal ion to soft tissue tumors. However, in the practice of the use of these conjugates a series of problems has been observed. For example, the problems have involved the fragile nature of the antibody, the slow clearance of the radioactivity from the blood stream, the uptake of radioactivity in non-target tissues such as liver and kidney, and the potential of an immune response of the patient to the injected protein.

Another approach to delivering metal ions to soft tissue cancers or tumors is by means of a metal ligand complex. Although this complex approach has not been pursued in the recent literature, it has received extensive attention in earlier literature. The recognition by Andrews et al. in *Radiology* 61, 570-599 (1953) that $Ga^{+3}$ had a tendency to localize in soft tissue tumors led to the development of $^{67}$Ga-citrate as a tumor imaging agent [R. L. Hayes, *Int. J. Nucl. Med. Biol.* 10(4), 257-251 (1983)]. Although $^{67}$Ga-citrate is presently used for detecting abscesses more than for tumor diagnosis, many clinicians prefer to use it over the monoclonal antibody conjugates for diagnosis. Even though $^{67}$Ga-citrate is widely used, it has various disadvantages. For example, the rate of blood clearance is slow, so that images are taken as much as 48 hours post injection with $^{67}$Ga-citrate [see *Int. J. Appl. Nucl. Med. Biol.* 8, 249-255 (1984)]. In addition, high uptake of the $^{67}$Ga-citrate in non-target tissues make images difficult to interpret [see *Curr. Concepts in Diagn. Nucl. Med.* 1(4), 3-12 (1984)].

In attempts to obtain more useful complexes for delivery of metal ions to soft tissue tumors, certain aminocarboxylic acid complexes have been used. For example, Karube et al. in *Chem. Pharm. Bull.* 30(7), 2529-2533 (1982) found that $^{99m}$Tc-ethylenediaminediacetic acid (EDDA) and $^{57}$Co-EDDA could be used to image tumors in experimental animals bearing Ehrlich tumors. However, $^{99m}$Tc complexes with other ligands were less effective. Some of the ligands tested with $^{99m}$Tc were iminodiacetic acid (IDA), methyliminodiacetic acid (MIDA), nitrilotriacetic acid (NTA), ethylenediaminetetraacetic acid (EDTA), and hydroxyethylethylenediaminetriacetic acid (HEDTA). Woolfenden et al. in *Int. J. Nucl. Med.* 10(4), 251-256 (1983) found that $^{153}$Sm-citrate and $^{153}$Sm-chloride had a high liver uptake and suggested the use of higher stability chelates, such as $^{153}$Sm-EDTA, could improve the tumor to liver ratio. More recently, J. Harvey Turner in *Eur. J. Nucl. Med.* 13, 432-438 (1987) studied $^{153}$Sm chelates including HEDTA. The $^{153}$Sm-HEDTA chelates used a 20 to 1 HEDTA to Sm molar ratio. Tumor uptake was found to be significantly less than that of $^{67}$Ga-citrate; liver dose was much greater than tumor dose. He concluded that "it is unlikely that effective therapy doses of Sm-153 can be delivered to melanoma tumors by these and similar chelates." He suggested the use of monoclonal antibodies with $^{153}$Sm. Another attempt to have complexes deliver metal ions to soft tissue tumors was made by Tsc et al. in *J. Nucl. Med.* 30, 202-208 (1989) where they studied $^{153}$Sm-EDTA at a 10 to 1 ligand to metal molar ratio. These researchers proved that the complex was stable and compared the use of high specific activity $^{153}$Sm (1.7 Ci/mG) to low specific activity $^{153}$Sm (1.1 mCi/mG) in mice bearing Lewis lung carcinoma. They proposed using the complex as an imaging agent using the high specific activity $^{153}$Sm. However, similar to what J. Harvey Turner reported, these researchers also found significant uptake in the liver as shown by their biodistribution and images.

Therefore, there is still a need for an adaquate system to deliver radionuclides selectively to soft tissue tumors.

Surprisingly, it has now been found that various radionuclide-HEDTA complexes, particularly the $^{153}$Sm-HEDTA complex, having a high ligand to metal molar ratio, such as from at least 50:1, give good soft tumor localization with no significant liver uptake and can be used as diagnostic or therapeutic agents.

SUMMARY OF THE INVENTION

The present invention concerns a method for the therapeutic and/or diagnostic treatment of a mammal having a soft tissue tumor which comprises administering to said mammal an effective amount of a composition comprising: (1) a complex which comprises a ligand and a metal ion wherein the ligand is hydroxyethylethylenediaminetriacetic acid or a pharmaceutically acceptable salt thereof and wherein the metal is $^{153}$Sm, $^{166}$Ho, $^{90}$Y, $^{159}$Gd, $^{177}$Lu, $^{111}$In, $^{115m}$In, $^{175}$Yb, $^{47}$Sc, $^{165}$Dy, $^{52}$Fe, $^{72}$Ga, $^{67}$Ga, $^{68}$Ga, Gd, or Fe and the ligand to metal molar ratio is at least 50:1, and (2) a physiologically acceptable liquid carrier.

DETAILED DESCRIPTION OF THE INVENTION

The method of this invention is used for the therapeutic and/or diagnostic treatment of a mammal having a soft tissue tumor. The compositions used in the method have a radionuclide or metal complexed with a chelating agent. As will be more fully discussed later, the properties of the radionuclide, of the chelating agent and of the complex formed therefrom are important considerations in determining the effectiveness of any particular composition employed for such treatment.

For the purposes of this invention, the term "tumor" shall denote a neoplasm, a new abnormal growth of tissue that is not inflammatory, which arises without obvious cause from cells of preexistent tissue, and generally possesses no physiologic function. Examples may include "carcinomas" which originate from epithelial cells, "sarcomas" of mesodermal (connective tissue) orgin, and lymphomas from the lymphatic system. The origin of the neoplasm is not critical to this invention.

As used herein, "complex" refers to a chelating agent complexed with a metal ion, preferably a +3 metal ion, especially a radioactive rare-earth type metal ion, wherein at least one metal atom is chelated or sequestered; "radioactive" when used in conjunction with the word "metal ion" refers to one or more isotopes of the rare-earth type elements the emit particles and/or photons. The term "radionuclide" or "metal" indicates the metal ion. When the ligand to metal ratio is discussed, the ratio is molar. The metal ligand complexes of this invention can consist of a formulation having the combination of 1 metal with 1 ligand in the form of a complex and having one or more complexes comprised of a different metal and/or different ligand, present in the same formulation. An example of this would be combining one metal ion that is a gamma emitting radionuclide for imaging with a ligand and also having present another metal that is a particle emitter for therapy with the same or different ligand. The combination of radionuclides may be more efficacious than either radionuclide alone. These combinations of complexes may be prepared by administering two complexes at about the same time to the mammal, or making each complex separately and mixing them prior to use, or mixing the two metal ions with the same ligand and preparing the two or more complexes concurrently.

The radionuclide used in the complex of the present invention may be suitable for therapeutic, diagnostic or both therapeutic and diagnostic purposes. Examples of the radionuclide used for diagnostic purposes are Fe, Gd, $^{111}$In, $^{67}$Ga, or $^{68}$Ga, especially preferred are $^{111}$In, or $^{67}$Ga. Examples of the radionuclide used for therapeutic purposes are $^{166}$Ho, $^{165}$Dy, $^{90}$Y, $^{115m}$In, $^{52}$Fe, or $^{72}$Ga, preferably $^{166}$Ho, or $^{90}$Y. For use for both therapeutic and diagnostic purposes the radionuclide used is $^{153}$Sm, $^{177}$Lu, $^{175}$Yb, $^{159}$Gd, or $^{47}$Sc, with $^{153}$Sm, $^{177}$Lu, or $^{175}$Yb being preferred.

Radionuclides can be produced in several ways. In a nuclear reactor, a nuclide is bombarded with neutrons to obtain a radionuclide, e.g.

$$\text{Sm-152} + \text{neutron} \rightarrow \text{Sm-153} + \text{gamma}.$$

Another method of obtaining radionuclides is by bombarding nuclides with linear accelerator or cyclotron-produced particles. Yet another way of obtaining radionuclides is to isolate them from fission product mixtures. The method of obtaining the radionuclide is not critical to the present invention.

To irradiate $Sm_2O_3$ for production of Sm-153, the desired amount of target is first weighed into a quartz vial, the vial is flame sealed under vacuum and welded into an aluminum can. The can is irradiated for the desired length of time, cooled for several hours and opened remotely in a hot cell. The quartz vial is removed and transferred to a glove box, crushed into a glass vial which is then sealed with a rubber septum and an aluminum crimp cap. One milliliter of 1–4M HCl is then added to the vial via syringe to dissolve the $Sm_2O_3$. Once dissolved, the solution is diluted to the appropriate volume by addition of water. The solution is removed from the original dissolution vial which contains shards of the crushed quartz vial and transferred via syringe to a clean glass serum vial. This solution is then used for complex preparation. Similar procedures are used to prepare $^{177}$Lu, $^{159}$Gd, and $^{166}$Ho. All radionuclides for this invention are either available commercially or are available from the reactor at the University of Missouri at Columbia.

When aqueous solutions of metal ions are mixed with solutions containing complexing agents, such as HEDTA, a complex between the metal ion and the ligand can be formed as shown by the equation below.

$$M + L \rightleftharpoons M \cdot L$$

The reaction is believed to be in equilibrium such that the concentrations of metal (M) and complexing agent, or ligand (L), can affect the concentration of species present in solution. Competing side reactions, such as metal hydroxide formation, can also occur in aqueous solution, thus $$xM + yOH^- \rightarrow M_x(OH)y.$$

The OH$^-$ concentration in solution, which is related to pH is, therefore, an important parameter to be considered. If the pH is too high, the metal tends to form metal hydroxides rather than complexes. The complexing agents may also be adversely affected by low pH. Complexation may require the loss of proton(s); therefore at low pH, conditions may not be favorable for complexation to occur. Consideration must be given to the solubility characteristics of the ligand, radionuclide, and complex. Although not limited thereto, a pH in the range of from 5 to 11 is preferred for complexation.

The chelating agent is hydroxyethylethylenediaminetriacetic acid (HEDTA) or a pharmaceutically acceptable salt thereof. HEDTA is available commercially from The Dow Chemical Company or may be prepared readily by methods known to those skilled in the art of organic synthesis such as shown in U.S. Pat. No. 2,811,557. For the purpose of the present invention, the complexes described herein and physiologically acceptable salts thereof are considered equivalent in the therapeutically effective compositions. Physiologically acceptable salts refer to the acid addition salts of those bases which will form a salt with at least one acid group of the ligand employed and which will not cause a significant adverse physiological effect when administered to a mammal at dosages consistent with good pharmacological practice. Suitable bases include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like, ammonia, primary, secondary and tertiary amines and the like. Physiologically acceptable salts may be prepared by treating the acid with an appropriate base.

The metal and ligand may be combined under any conditions which allow the two to form a complex. Generally, mixing in water at a controlled pH (the choice of pH is dependent upon the choice of metal) is all that is required. Most of the complexes employed in this invention were prepared as follows: the desired amount of HEDTA (trisodium salt) was placed in a vial and dissolved by addition of water. The appropriate amount of the samarium, or other radionuclide, in the stock solution described above was then added to the HEDTA solution. The pH of the resulting solution was then adjusted to the appropriate level (usually 7–8). Additionally, the complex used in this invention may be a mixture of the different metals as described under the complex term before.

In the method of this invention, it is necessary to employ the complex in the presence of an excess of ligand. The ligand to metal ratio (L:M) of the ligand HEDTA to radionuclide or metal is at least 50:1. The upper limit of L:M depends on the toxicity of the ligand HEDTA or the specific activity of the radionuclide. The preferred range for the L:M ratio is from 50:1 to about 600:1, preferably from about 100:1 to about 500:1, especially about 250:1 to about 300:1. When the radionuclide is used in the no carrier added form, then the upper L:M range could be significantly higher, such as $5 \times 10^7:1$.

As used herein, the term "mammal" means animals that nourish their young with milk secreted by mammary glands, preferably warm blooded mammals, more preferably humans.

As used herein, "pharmaceutically acceptable salt" means any salt of HEDTA which is sufficiently nontoxic to be useful in therapy or diagnosis of mammals. Thus, the salts are useful in accordance with this invention. Representative of those salts, which are formed by standard reactions, from both organic and inorganic sources include, for example, sulfuric, hydrochloric, phosphoric, acetic, succinic, citric, lactic, maleic, fumaric, palmitic, cholic, palmoic, mucic, glutamic, d-camphoric, glutaric, glycolic, phthalic, tartaric, formic, lauric, steric, salicylic, methanesulfonic, benzenesulfonic, sorbic, picric, benzoic, cinnamic acids and other suitable acids. Also included are salts formed by standard reactions from both organic and inorganic sources such as ammonium, alkali metal ions, alkaline earth metal ions, and other similar ions. Particularly preferred are the salts of the compounds of HEDTA where the salt is calcium, magnesium, potassium, sodium, ammonium, or mixtures thereof.

The formulations of the present invention are in the solid or liquid form containing the active radionuclide complexed with the ligand. These formulations may be in kit form such that the two components (i.e. ligand and metal) are mixed at the appropriate time prior to use. Whether premixed or as a kit, the formulations usually require a pharmaceutically acceptable carrier.

Injectable compositions of the present invention may be either in suspension or solution form. In the preparation of suitable formulations it will be recognized that, in general, the water solubility of the salt is greater than the acid form. In solution form the complex (or when desired the separate components) is dissolved in a physiologically acceptable carrier. Such carriers comprise a suitable solvent, preservatives such as benzyl alcohol, if needed, and/or buffers. Useful solvents include, for example, water, aqueous alcohols, glycols, and phosphate or carbonate esters. Such aqueous solutions contain no more than 50 percent of the organic solvent by volume.

Injectable suspensions are compositions of the present invention that require a liquid suspending medium, with or without adjuvants, as a carrier. The suspending medium can be, for example, aqueous polyvinylpyrrolidone, inert oils such as vegetable oils or highly refined mineral oils, or aqueous carboxymethylcellulose. Suitable physiologically acceptable adjuvants, if necessary to keep the complex in suspension, may be chosen from among thickeners such as carboxymethylcellulose, polyvinylpyrrolidone, gelatin, and the alginates. Many surfactants are also useful as suspending agents, for example, lecithin, alkylphenol, polyethylene oxide adducts, naphthalenesulfonates, alkylbenzenesulfonates, and the polyoxyethylene sorbitan esters.

Many substances which affect the hydrophilicity, density, and surface tension of the liquid suspension medium can assist in making injectable suspensions in individual cases. For example, silicone antifoams, sorbitol, and sugars are all useful suspending agents.

An "effective amount" of the formulation is used for therapy. The dose will vary depending on the disease being treated. Although in vitro diagnostics can be performed with the formulations of this invention, in vivo diagnostics are also contemplated using formulations of this invention. The invention described herein provides a means of delivering a therapeutic amount of radioactivity to soft tissue tumors. However, it may also be desirable to administer a "sub-therapeutic" amount to determine the fate of the radionuclide using a scintillation camera prior to administering a therapeutic dose or if diagnostic images are the desired result. Therapeutic doses will be administered in sufficient amounts to reduce pain and/or inhibit tumor growth and/or cause regression of tumors and/or kill the tumor. Amounts of radionuclide needed to provide the desired therapeutic dose will be determined experimentally and optimized for each particular composition. The amount of radioactivity required to deliver a therapeutic dose will vary with the individual composition employed. The composition to be administered may be given in a single treatment or fractionated into several portions and administered at different times. Administering the composition in fractionated doses may make it possible to minimize damage to non-target tissue. Such multiple dose administration may be more effective.

The compositions of the present invention may be used in conjunction with other active agents and/or ingredients that enhance the therapeutic effectiveness of the compositions and/or facilitate easier administration of the compositions.

Studies to determine the qualitative biodistribution of the various radionuclides were conducted by injecting the compositions into miniature pigs having melanotic lesions, which occur spontaneously. $^{67}$Ga-citrate was used as the control and was given by the same route of administration as the test samples.

While not wishing to be bound by theory, it is believed that the advantageous results of the present invention are obtained because of the possible uptake preferentially in the tumor. The mechanism of uptake of the radionuclide by neoplastic tissue is not clear. Some suggested mechanisms are:
a) An imbalance between arterial blood supply to the tumor and venous drainage from the tumor. A reduced venous drainage would result in an increase in concentration of the material within the tumor mass.
b) Lymphatic drainage from a tumor may be decreased.
c) Non-specific binding to protein within the tumor may occur.
d) Because inflammatory reaction is usually present near a tumor, this may result in the differential concentration of radiolabel within the tumor.
e) MetallothionEin a protein binder of heavy metals.
f) Several mechanisms may be involved.

Although the theory for the mechanism of action is still unknown, the present invention provides a complex which allows metal ions to locate in the tumor and displays low uptake in other tissues, e.g. liver.

The following definitions are provided for some terms that are used throughout this text.

Glossary

Conc. = concentrated;
mG = milligrams
mCi = milliCuries
HEDTA = Hydroxyethylethylenediaminetriacetic acid
Sm = Samarium
Ho = Holmium
Yb = Ytterbium
Y = Yttrium
Gd = Gadolinium
Lu = Lutetium
In = Indium
Sc = Scandium
Fe = iron
Ga = Gallium
chelant is equivalent to ligand;
complex is equivalent to chelate; and
L:M = ligand to metal molar ratio.

The invention will be further clarified by a consideration of the following examples, which are intended to be purely exemplary of the present invention.

EXAMPLE A

Comparative A

HETDA.3Na.H$_2$O, 6.9 mG, was weighed into a 5 mL glass vial, then 2.38 mL of a 3×10$^{-4}$M solution of SmCl$_3$ in 0.1M HCl and 0.62 mL of a 3×10$^{-4}$M solution of $^{153}$SmCl$_3$ in 0.1M HCl was added. The pH was adjusted using the procedure of Example 1. The activity of the final solution was about 3.5 mCi in about 3.0 mL with a L:M ratio of 20:1.

EXAMPLE 1

HETDA.3Na.H$_2$O, 102.8 mG, was weighed into a 5 mL glass vial, then 1.96 mL of a 3×10$^{-4}$M solution of SmCl$_3$ in 0.1M HCl and 1.54 mL of a 3×10$^{-4}$M solution of $^{153}$SmCl$_3$ in 0.1M HCl was added. The pH was adjusted to 11–12 with 15 µL of 50% NaOH. The pH was then lowered to 7–8 with 25 µL of 3.0M HCl followed by 2 µL of conc. HCl. The activity of the final solution was about 6.0 mCi in about 3.5 mL with a L:M ratio of about 257:1.

EXAMPLE 2

The HEDTA solutions prepared in Examples 1 and A were evaluated in miniature pigs having naturally occurring melanomic lesions. Each injected solution was from 0.5–1 mL having 1–2 mCi of $^{153}$Sm present. Each pig had whole body counts immediately after injection and again at 24, 48 and 72 hours.

Images of each pig (right lateral, left lateral and dorsal) were taken at 4, 24, 48 and 72 hours. The 24 hour images were evaluated independently by 3 investigators using the following scheme for the uptake of $^{153}$Sm in various tissues:
0 = No discernible uptake
1 = Slight uptake (negligible)
2 = Moderate uptake (intermediate)
3 = Definite uptake (high)

The tissues evaluated were bone, liver and tumor. The average of the scoring of the 3 independent investigators is given in the following table:

TABLE I

| Example | L/M Ratio | % Whole Body Retention (72 hrs.) | Bone Uptake (72 hr) | Liver Uptake (72 hrs) | Tumor Uptake (Location) |
|---|---|---|---|---|---|
| A | 20 | 96.0 | 2.67 | 2.67 | 0.00 (Left thigh) |
| A | 20 | 91.9 | 3.00 | 2.67 | 2.00 (Right thorax) |
|   |    |      |      |      | 0.00 (Left Hip) |
| 1 | 257 | 75.5 | 3.00 | 1.00 | 2.00 (Leg) |
|   |    |      |      |      | 0.00 (Body) |
| 1 | 257 | 70.9 | 3.00 | 1.00 | 0.33 (Left nasal) |
|   |    |      |      |      | 0.00 (Left elbow) |

% = the percentage of injected dose

Compound A is comparative and Example 1 is a complex of the invention.

The above data shows that when the ligand/metal ratio is high, then the tumor uptake remains about the same, but whole body retention and the liver uptake significantly drop. Because of these uptake differences, the images are vastly improved for the higher ligand to metal ratio injections.

EXAMPLE B

Comparative B

When $^{67}$Ga-citrate (purchased from Syncor) was used in a procedure similar to Example 2, the results obtained are shown in the following table:

TABLE II

| Example | % Whole Body Retention (72 hrs.) | Bone Uptake (72 hr) | Liver Uptake (72 hrs) | Tumor Uptake (Location) |
|---|---|---|---|---|
| B | 98.5 | 1.00 | 3.00 | 0.00 (Left sacrum) |
| B | 96.7 | 1.00 | 2.67 | 0.33 (Right head) 1.67 (Draining node) |
| B | 97.1 | 1.00 | 3.00 | 3.00 (Left head) 3.00 (Right thorax) 2.00 (Right stifle) |

$^{67}$Ga-citrate never cleared the extra-cellular fluid and had an unacceptably large liver uptake. Although tumor uptake was noted, the degree of uptake was similar to the degree of uptake of non-target tissue. Thus, the tumor image was almost indistinguishable from the high background radiation.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A method for the therapeutic and/or diagnostic treatment of a mammal having a non-calcific tissue tumor which comprises administering to said mammal an effective amount of a composition comprising: (1) a complex which comprises a ligand and a metal wherein the ligand is hydroxyethylethylenediaminetriacetic acid or a pharmaceutically acceptable salt thereof and wherein the metal ion is $^{153}$Sm, $^{166}$Ho, $^{90}$Y, $^{165}$Dy, $^{159}$Gd, $^{177}$Lu, $^{111}$In, $^{115m}$In, $^{175}$Yb, $^{47}$Sc, $^{52}$Fe, $^{72}$Ga, $^{67}$Ga, or $^{68}$Ga and the ligand to metal molar ratio is 100:1 to about 500:1, and (2) a physiologically acceptable liquid carrier.

2. A method of claim 1 for therapeutic treatment.

3. The method of claim 2 wherein the metal is $^{166}$Ho, $^{90}$Y, $^{175}$Yb, $^{165}$Dy, $^{115m}$In, $^{52}$Fe, or $^{72}$Ga.

4. A method of claim 1 for diagnostic treatment.

5. The method of claim 4 wherein the metal is $^{111}$In, $^{67}$Ga, $^{68}$Ga.

6. The method of claim 1 for therapeutic and diagnostic treatment.

7. The method of claim 6 wherein the metal is $^{153}$Sm, $^{177}$Lu, $^{175}$Yb, $^{159}$Gd, or $^{47}$Sc.

8. The method of claim 7 wherein the metal is $^{153}$Sm.

9. A method of claim 1 wherein the ligand to metal molar ratio is from 250:1 to about 300:1.

10. A method of claim 1 wherein the metal used is in the no carrier added form.

11. A method of claim 10 wherein the ligand to metal molar ratio is about $5 \times 10^7$:1.

12. The method of claim 1 wherein the physiologically acceptable liquid carrier is water and the resulting solution is adjusted to have a pH of about 7 to about 8.

13. The method of claim 1 wherein the ligand is in the form of its sodium salt.

14. The method of claim 1 wherein the composition administered to a mammal contains 2 or more different radioisotopes.

* * * * *